US012303916B2

(12) United States Patent
Yamashita et al.

(10) Patent No.: US 12,303,916 B2
(45) Date of Patent: May 20, 2025

(54) PEPTIDE AND METHOD FOR USING SAME (71) Applicants: Shibaura Institute of Technology, Tokyo (JP); JX ADVANCE METALS CORPORATION, Tokyo (JP)

(72) Inventors: Mitsuo Yamashita, Tokyo (JP); Akira Miura, Hitachi (JP)

(73) Assignees: SHIBAURA INSTITUTE OF TECHNOLOGY, Tokyo (JP); JX ADVANCED METALS CORPORATION, Tokyo (JP)

( * ) Notice: Subject to any disclaimer, the term of this patent is extended or adjusted under 35 U.S.C. 154(b) by 973 days.

(21) Appl. No.: 17/288,095

(22) PCT Filed: Oct. 17, 2019

(86) PCT No.: PCT/JP2019/040997
§ 371 (c)(1),
(2) Date: Apr. 23, 2021

(87) PCT Pub. No.: WO2020/085219
PCT Pub. Date: Apr. 30, 2020

(65) Prior Publication Data
US 2023/0285986 A1   Sep. 14, 2023

(30) Foreign Application Priority Data
Oct. 24, 2018  (JP) .................................. 2018-200143

(51) Int. Cl.
*C07K 7/08* (2006.01)
*B03D 1/018* (2006.01)
*B03D 1/02* (2006.01)
*C12N 15/70* (2006.01)

(52) U.S. Cl.
CPC .............. *B03D 1/018* (2013.01); *B03D 1/02* (2013.01); *C07K 7/08* (2013.01); *C12N 15/70* (2013.01)

(58) Field of Classification Search
CPC ...... B03D 1/018; B03D 1/02; B03D 2203/02; C07K 7/08
See application file for complete search history.

(56) References Cited

U.S. PATENT DOCUMENTS

| | | | |
|---|---|---|---|
| 2011/0094942 A1 | 4/2011 | Ochi et al. | |
| 2012/0216318 A1 | 8/2012 | La Rosa et al. | |
| 2013/0004389 A1* | 1/2013 | Okamoto | ............ C22B 15/0008 423/26 |

FOREIGN PATENT DOCUMENTS

| | | |
|---|---|---|
| AU | 2011318944 B2 | 4/2012 |
| CN | 105039333 A | 11/2015 |
| JP | 2010-133004 A | 6/2010 |
| JP | 2011-156521 A | 8/2011 |
| JP | 2012-87400 A | 5/2012 |
| WO | WO 2018/052134 A1 | 3/2018 |

OTHER PUBLICATIONS

Sovago (Coordination Chemistry Reviews, 2012, 256, 2225-2233) (Year: 2012).*
Curtis (Biotechnology and Bioengineering, vol. 114, No. 5, May 2017, 998-1005) (Year: 2017).*
International Preliminary Report on Patentability and English translation of the Written Opinion of the International Searching Authority (Forms PCT/IB/338, PCT/IB/373, PCT/ISA/237) for International Application No. PCT/JP2019/040997, dated May 6, 2021.
International Search Report for PCT/JP2019/040997 (PCT/ISA/210) mailed on Jan. 7, 2020.
Written Opinion of the International Searching Authority for PCT/JP2019/040997 (PCT/ISA/237) mailed on Jan. 7, 2020.
Australian Office Action dated Jun. 9, 2022 for corresponding Application No. 2019366084.
GenBank, "phototropin [Scouleria aquatica]", GenBank Accession No. AHZ63889, May 19, 2014, pp. 1-2.
Li et al., "Horizontal transfer of an adaptive chimeric photoreceptor from bryophytes to ferns", PNAS, vol. 111, No. 18, May 6, 2014, pp. 6672-6677.

* cited by examiner

*Primary Examiner* — Sudhakar Katakam
(74) *Attorney, Agent, or Firm* — Birch, Stewart, Kolasch & Birch, LLP (57) ABSTRACT

Provided is a method for selecting arsenic-containing minerals.
A peptide comprising an amino acids sequence according to the following formula:

(T,S,N,Q)-(L,I,V,F,A)-(E,D)-(R,K,N,M,D,C,P,Q,S,E,
T,G,W,H,Y)-(L,I,V,F,A)-(R,K,N,M,D,C,P,Q,S,E,
T,G,W,H,Y)-(L,I,V,F,A)-(L,I,V,F,A)-(L,I,V,F,A)-
(R,H,K)-(T,S,N,Q)-(T,S,N,Q)

wherein one amino acid is respectively selected from each group defined by paired parentheses.

2 Claims, 2 Drawing Sheets

Specification includes a Sequence Listing.

PEPTIDE AND METHOD FOR USING SAME

REFERENCE TO SEQUENCE LISTING SUBMITTED VIA EFS-WEB

This application includes an electronically submitted sequence listing in .txt format. The .txt file contains a sequence listing entitled "5526-0178PUS1_ST25.txt" created on Oct. 17, 2021 and is 830 bytes in size. The sequence listing contained in this .txt file is part of the specification and is hereby incorporated by reference herein in its entirety.

TECHNICAL FIELD

The present invention is related to a novel peptide and use thereof.

BACKGROUND ART

Some mineral resources contain valuable metals while they may contain harmful substances. For example, a copper mineral that is mainly produced from copper mine is a sulfide mineral. This sulfide mineral may be roughly classified into secondary sulfide minerals (which contains a relatively high amount of copper, and mainly contains minerals such as chalcocite ($Cu_2S$) and covellite (CuS)) and a primary sulfide mineral (which contains a relatively low amount of copper and mainly contains such as chalcopyrite ($CuFeS_2$)). In addition to these minerals, this sulfide mineral also includes arsenic-containing minerals (such as enargite).

Arsenic, which is harmful to environment, may cause various problems when refining sulfide minerals that are contaminated with arsenic-containing minerals. Therefore, arsenic is conventionally removed via various techniques prior to refining. For example, Japanese Patent Publication No 2012-087400 teaches roasting to evaporate arsenic for the purpose of removing arsenic from minerals in advance.

Japanese Patent Publication No 2010-133004 teaches using sodium thiosulfate as a depressant for the purpose of isolating arsenic-containing minerals from minerals containing copper and arsenic.

Japanese Patent Publication No 2011-156521 teaches froth flotation with use of chelate as a depressant (such as polyethylene amine) for the purpose of removing arsenic from minerals containing copper and arsenic.

Furthermore, WO2018/052134 discloses repeating panning for screening thereby obtaining phage which can bind to Enargite. Moreover, this patent document discloses a peptide that is expressed on the surface of the phage and can bind to Enargite.

CITATION LIST

Patent Literature

[PTL 1] Japanese Patent Publication No 2012-087400
[PTL 2] Japanese Patent Publication No 2010-133004
[PTL 3] Japanese Patent Publication No 2011-156521
[PTL 4] WO 2018/052134

SUMMARY OF INVENTION

Technical Problem to be Solved

In conventional methods such as roasting to evaporate arsenic for removal as taught in Patent literature 1, a large scale of facility has been required. Furthermore, some minerals are difficult to be physically deprived of arsenic. Especially, it is quite often that copper minerals mainly containing such as chalcopyrite and bornite, and copper minerals mainly containing such as chalcocite also contain arsenic-containing minerals such as tennantite $((CuFe)_{12}As_4S_{13})$ and enargite ($Cu_3AsS_4$). Furthermore, these minerals containing both arsenic and copper has a feature for froth flotation that is similar to those of chalcopyrite and bornite. Thus, it is difficult to separate via froth flotation arsenic-containing minerals from copper-containing minerals. Regarding the methods using sodium thiosulfate according to Patent literature 2 or chelate according to Patent literature 3, separation of arsenic-containing minerals from copper-containing minerals is insufficient and these methods have not been practically used. Patent literature 4 discloses on the basis of bubble-pick-up test that a certain peptide can bind to Enargite, and thereby hydrophilize the surface of Enargite. However, in a practical environment for isolating Enargite, various factors may prevent from biding to Enargite, and thus, there is a need for a peptide that can bind to Enargite under even more severe conditions.

An object of the present invention is to provide novel methods for efficiently isolating arsenic-containing minerals.

Solution to Problem

In light of the above object, the present inventors have studied intensively and found that a certain peptide and phages having the certain peptide can bind to arsenic-containing minerals.

On the basis of the above discovery, in one aspect, the present invention includes the following inventions.

(Invention 1)

A peptide comprising an amino acids sequence according to the following formula:

(T,S,N,Q)-(L,I,V,F,A)-(E,D)-(R,K,N,M,D,C,P,Q,S,E,
T,G,W,H,Y)-(L,I,V,F,A)-(R,K,N,M,D,C,P,Q,S,E,
T,G,W,H,Y)-(L,I,V,F,A)-(L,I,V,F,A)-(L,I,V,F,A)-
(R,H,K)-(T,S,N,Q)-(T,S,N,Q)

wherein one amino acid is respectively selected from each group defined by paired parentheses.

(Invention 2)

A peptide comprising the following sequence:

```
                                    (SEQ ID NO: 1)
Ser-Leu-Asp-Gly-Ala-Gly-Ala-Ala-Leu-Arg-Thr-Ser.
```

(Invention 3)

A peptide according to the following sequence:

```
                                    (SEQ ID NO: 1)
Ser-Leu-Asp-Gly-Ala-Gly-Ala-Ala-Leu-Arg-Thr-Ser.
```

(Invention 4)

A peptide comprising a sequence which is at least 75% identical to the following sequence:

```
                                    (SEQ ID NO: 1)
Ser-Leu-Asp-Gly-Ala-Gly-Ala-Ala-Leu-Arg-Thr-Ser.
```

(Invention 5)

A peptide comprising a sequence which is at least 83% identical to the following sequence:

(SEQ ID NO: 1)
Ser-Leu-Asp-Gly-Ala-Gly-Ala-Ala-Leu-Arg-Thr-Ser.

(Invention 6)

A peptide comprising a sequence which is at least 90% identical to the following sequence:

(SEQ ID NO: 1)
Ser-Leu-Asp-Gly-Ala-Gly-Ala-Ala-Leu-Arg-Thr-Ser.

(Invention 7)

A peptide comprising a sequence derived from the following sequence by inserting, deleting, replacing, and/or adding 1-5 amino acid:

(SEQ ID NO: 1)
Ser-Leu-Asp-Gly-Ala-Gly-Ala-Ala-Leu-Arg-Thr-Ser.

(Invention 8)

A composition for selecting and/or identifying a mineral containing arsenic, the composition comprising the peptide of any one of Inventions 1-7.

(Invention 9)

A nucleic acid encoding the peptide of any one of Inventions 1-7.

(Invention 10)

A nucleic acid comprising a sequence which is at least 90% identical to a nucleic acid sequence encoding the peptide of any one of Inventions 1-7.

(Invention 11)

A nucleic acid being capable of hybridizing under a stringent condition with a sequence being complementary to a nucleic acid encoding the peptide of any one of Inventions 1-7.

(Invention 12)

A microorganism comprising on its surface the peptide of any one of Inventions 1-7.

(Invention 13)

A microorganism comprising the nucleic acid of any one of Inventions 9-11.

(Invention 14)

A particle comprising on its surface the peptide of any one of Inventions 1-7.

(Invention 15)

A purification column comprising the peptide of any one of Inventions 1-7.

(Invention 16)

A collector for use of froth flotation comprising the peptide of any one of Inventions 1-7.

(Invention 17)

A depressant for use of froth flotation comprising the peptide of any one of Inventions 1-7.

(Invention 18)

A method for isolating a mineral containing arsenic, the method comprising using the peptide of any one of Inventions 1-7.

(Invention 19)

A method for selecting and/or identifying a mineral containing arsenic, the method comprising using the peptide of any one of Inventions 1-7 or the composition of Invention 8.

(Invention 20)

A method of Invention 19, the method comprising:
adding a microorganism into mineral dispersion, wherein the microorganism comprises the peptide on its surface and wherein the mineral contains arsenic;
aggregating and precipitating the mineral; and
recovering the aggregated and precipitated mineral.

(Invention 21)

A method of Invention 19, the method comprising:
affixing the peptide to a carrier;
introducing the carrier into a column for chromatography; and
passing mineral dispersion through the column, wherein the mineral contains arsenic.

(Invention 22)

A method of Invention 19, the method comprising:
affixing the peptide to a particle; and
introducing the particle into mineral dispersion, wherein the mineral contains arsenic.

(Invention 23)

A method of Invention 19, the method comprising froth floating with use of the peptide.

(Invention 24)

A method of Invention 23, the froth floating comprising:
introducing a mixture, the mixture containing:
the mineral containing arsenic; and
pyrite and/or chalcopyrite; and
introducing the peptide and/or the microorganism containing the peptide as a depressant,
whereby the mineral containing arsenic is sorted to flotation tailings and the pyrite and/or chalcopyrite is sorted to concentrate.

(Invention 25)

A method of Invention 24, wherein the mineral containing arsenic is enargite and the microorganism is phage.

(Invention 26)

A method of Invention 24 or 25, the froth floating comprising:
after introducing the peptide and/or the microorganism containing the peptide as a depressant, further introducing a collector.

Advantageous Effects of Invention

In one aspect, the present invention utilizes a peptide. Thereby, it does not require a large scale of devices comparing to conventional techniques.

Furthermore, the peptides according to the present invention enable to isolate a mineral of interest efficiently.

DESCRIPTION OF EMBODIMENTS

Now, for the purpose of enhancing the understanding of the present invention, more specified embodiments are described hereinafter, which are not intended to limit the scope of the present invention.

1. Applicable Substances

In one embodiment, the present invention is applicable to a method for isolating certain substances. The certain substances may include arsenic-containing minerals. More specifically, the certain substances may include minerals containing both arsenic and copper. The minerals containing both arsenic and copper may include enargite and tennantite, etc.

2. Peptide

For the purpose of isolating the substances described above, in one embodiment of the present invention, a peptide can be used. More specifically, a peptide can be used that includes an amino-acids sequence according to the following formula (1). Additionally, a certain number of amino acid can be added in their N terminal and/or C terminal. The certain number may fall within the numerical range defined by two numbers selected from 1, 2, 3, 4, 5, 6, 7, 8, 9, 10, 15, and 20 (e.g., from 1 to 10, or from 5 to 20).

(T,S,N,Q)-(L,I,V,F,A)-(E,D)-(R,K,N,M,D,C,P,Q,S,E,
T,G,W,H,Y)-(L,I,V,F,A)-(R,K,N,M,D,C,P,Q,S,E,
T,G,W,H,Y)-(L,I,V,F,A)-(L,I,V,F,A)-(L,I,V,F,A)-
(R,H,K)-(T,S,N,Q)-(T,S,N,Q)     (1)

(wherein one amino acid is respectively selected from each group defined by paired parentheses)

The working examples described hereinafter show the peptide according to the following amino acid sequence was used to isolate enargite.

The above amino acid sequence of (1) and the above amino acid sequence of (2) correspond to each other as follows.

TABLE 1

| | (2) | (1) |
|---|---|---|
| 1 | Ser | T, S, N, Q |
| 2 | Leu | L, I, V, F, A |
| 3 | Asp | E, D |
| 4 | Gly | R, K, N, M, D, C, P, Q, S, E, T, G, W, H, Y |
| 5 | Ala | L, I, V, F, A |
| 6 | Gly | R, K, N, M, D, C, P, Q, S, E, T, G, W, H, Y |
| 7 | Ala | L, I, V, F, A |
| 8 | Ala | L, I, V, F, A |
| 9 | Leu | L, I, V, F, A |
| 10 | Arg | R, H, K |
| 11 | Thr | T, S, N, Q |
| 12 | Ser | T, S, N, Q |

As shown in Table 1, the first amino acid in the sequence (2) is serine. This is a polar non-charged amino acid. Thus, even if replacing with threonine, asparagine, or glutamine, which are also polar non-charged amino acids, the peptide will retain same or similar property. Also, the twelfth amino acid serine and the eleventh amino acid threonine in the sequence (2) can be replaced in a similar manner to retain same or similar property.

The second amino acid in the sequence (2) is leucine, which has a hydrophobic amino acid. Thus, even if replacing with isoleucine, valine, phenylalanine, or alanine, etc., all of which have also hydrophobic residue, the peptide will retain same or similar property. Also, the ninth amino acid leucine or the fifth, seventh, and eighth amino acid alanine in the sequence (2) can be replaced in a similar manner to retain same or similar property.

The third amino acid in the sequence (2) is aspartic acid, which is an acidic amino acid. Thus, even if replacing with glutamic acid, which is also an acidic amino acid, the peptide will retain same or similar property.

The fourth amino acid in the sequence (2) is glycine. Since the residue of glycine is (—H), it is not likely that the residue itself contributes to a certain function. Thus, even if replacing glycine with the other natural amino acids, the peptide will retain same or similar property. Also, the sixth amino acid glycine in the sequence (2) can be replaced in a similar manner to retain same or similar property.

The tenth amino acid in the sequence (2) is arginine, which has a basic residue. Thus, even if replacing with lysine or histidine, which are also basic amino acids, the peptide will retain same or similar property.

In one embodiment, the present invention encompasses the peptides including the following sequence.

Additionally, an arbitrary number of amino acid can be added in its N terminal and/or C terminal. Typically, the arbitrary number may fall within the numerical range defined by two numbers selected from 1, 2, 3, 4, 5, 6, 7, 8, 9, 10, 15, and 20 (e.g., from 1 to 10, or from 5 to 20).

In one embodiment, the present invention encompasses the peptides represented by the following 12-amino acid sequence.

```
                                    (SEQ ID NO: 1)
(2) Ser-Leu-Asp-Gly-Ala-Gly-Ala-Ala-Leu-Arg-Thr-
Ser
```

Regarding the above amino acid sequence (2), even if making a slight modification (e.g., insertion, replacement, and/or addition of amino acid), the modified peptide will retain property that is the same as or similar to that of amino acid sequence (2). For example, a peptide or a peptide including a sequence which is 66% or more, 75% or more, 83% or more, 90% or more, 95% or more, 98% or more, or 99% or more identical to the amino acids sequence (2), will also retain the same or similar property.

A numerical value for sequence similarity can be calculated by a technique known in the art. For example, the value may be calculated based on a value derived by Blastp, which is used for homology search of amino acids (or protein) and is provided by BLAST (Trademark).

In one embodiment, the present invention encompasses a peptide comprising a sequence derived from the following sequence by deleting, replacing, and/or adding 1-5 amino acids, typically, by deleting, replacing, and/or adding 4 or less, 3 or less, or 2 or less amino acids.

```
                                    (SEQ ID NO: 1)
(2) Ser-Leu-Asp-Gly-Ala-Gly-Ala-Ala-Leu-Arg-Thr-
Ser
```

In one embodiment, the present invention encompasses a composition containing the above peptides. In other words, not only the above peptides, but also a composition containing at least any one of the above peptides together with other ingredients can achieve the same or similar functions. The composition may contain arbitrary ingredients (e.g., buffer, NaCl, sugar, etc.) on the condition that they do not deteriorate the functions of the above peptides.

3. Nucleic Acid Encoding Peptide

In one embodiment, the present invention encompasses a nucleic acid encoding at least any one of the above peptides. The nucleic acid may be DNA or RNA. In one embodiment, the present invention encompasses a nucleic acid having a sequence being complementary to a sense strand encoding at least any one of the above peptides.

In one embodiment, the present invention encompasses a nucleic acid comprising a sequence which is at least 80% or more, 85% or more, 90% or more, 95% or more, or 98% or more identical to a nucleic acid sequence encoding at least any one of the above peptides. As similar to the case of amino acids sequence, a numerical value for sequence similarity can be calculated by a technique known in the art. For example, the value may be calculated based on a value derived from a search result by Blastn, which is provided by BLAST.

Moreover, in one embodiment, the present invention encompasses a nucleic acid being capable of hybridizing with a sequence being complementary to sense strand of a nucleic acid encoding at least any one of the above peptides. More specifically, the present invention encompasses the nucleic acid being capable of hybridizing under stringent condition. The stringent condition may be a condition known in the art. For example, it may be a condition that is disclosed in Japanese patent publication No. 2015-023831. More specifically, it may be judged through the following procedure: using a filter in which DNA is fixed; hybridization in the presence of 0.7-1.0 M of NaCl under the temperature 65 degree Celsius; and washing a filter at the temperature of 65 degree Celsius, by 0.1-2×SSC (saline-sodium citrate) solution (1×SSC solution contains 150 mM NaCl, 15 mM Sodium citrate).

Any of the above-described nucleic acids are usable for preparing a peptide of interest through a genetic engineering technique. For example, any one or more of the above-described nucleic acids may be introduced into an expression vector to express a peptide of interest in a large scale. Alternatively, a phage having a peptide of interest on its surface may be prepared through a phage display method described hereinafter.

4. Usage of Peptide and/or Nucleic Acid

The above-described peptides and/or nucleic acids may be applicable in various ways.

4-1. Microorganism

For example, utilizing genetic engineering technique (e.g., introducing at least any one of the above nucleic acids into genome of a microorganism), the microorganism may produce a peptide of interest in a large scale. Alternatively, expressing a peptide of interest in a surface of a microorganism, a substance of interest may be isolated with use of the microorganism. The term "microorganism" described herein includes organisms belonging to fungi, monera, or protist of the five-kingdom system. Also, the term "microorganism" described herein includes a virus, though it does not belong to an organism in a strict classification. Typically, fungi, bacteria, or a virus may be used. Preferably, a microorganism may be used in which genetic engineering procedure is established (e.g., yeast, *E. coli, lactobacillus*, a bacteriophage). In one embodiment, the present invention encompasses such microorganisms.

4-2. Particle

In one embodiment, the present invention encompasses a particle having a peptide on its surface. The peptide may be any one of the above-described peptides. The particle may be beads (e.g., magnetic beads, glass beads, high-molecular weight beads) or carrier etc. The size of a particle is not limited and may be adjusted depending on its usage. A peptide may be bound to a surface of a particle by a technique known in the art.

In one embodiment of the present invention, a substance of interest may be isolated with use of a particle having at least any one of the above peptides on its surface. For example, via the method described hereinafter, a substance of interest may be bound to the peptides and precipitated to be isolated.

4-3. Column for Purification

A substance of interest may be isolated via column chromatography. Column chromatography relies on a property where a column (or functional groups on an inner surface of the column) selectively binds to a certain substance. In one embodiment of the present invention, the above-described peptides can be affixed to a carrier, and then the carrier may be introduced into a column. Utilizing such a column, a substance of interest may be isolated.

4-4. Collector or Frother for Froth Flotation

Froth flotation is a method for separation by trapping particles via bubble. In this method, a collector or a frother may be used. In one embodiment, a peptide of the present invention may be bound to a collector or a frother known in the art such that it may be prone to be trapped by a bubble. Alternatively, such a peptide may be bound to a chemical moiety that renders hydrophobicity (e.g., alkyl group, phenyl group, a hydrophobic amino acid, etc.) thereby working as a collector such that it may be prone to be trapped by a bubble. Thereby, a substance of interest may be trapped by a bubble and consequently be isolated.

4-5. Depressant for Froth Flotation

In another embodiment, a peptide of the present invention can hydrophilize the surface of certain minerals. Thereby, it enables to inhibit the certain minerals floating in process of froth flotation. The peptide of the present invention therefore may be used as a depressant. In this regard, the peptide per se may be used, alternatively, the peptide bound to a certain microorganism may be used, and alternatively, the peptide bound to a certain chemical compound may be used.

5. Embodiment for Application (Methods for Isolation)

Now methods for the above application are described hereinafter.

5-1. Substances to be Isolated

The above-described embodiments for application are related to isolating a certain substance. For example, the above described arsenic-containing mineral (e.g., enargite) may be isolated. In one embodiment, a peptide of the present invention can more specifically bind to arsenic-containing minerals even in the presence of any substance that inhibits peptide-binding (e.g., impurity, surfactant, etc.).

5-2. A Method with Use of a Microorganism

In one embodiment of the present invention, using a microorganism, a substance (specifically, arsenic-containing mineral, more specifically, enargite) may be isolated. Regarding a microorganism, any of the above-described microorganisms may be used. Typically, a bacteriophage may be used.

Regarding procedure, initially, by a technique of genetic engineering known in the art, a nucleic acid sequence encoding the above-described peptides may be introduced into a microorganism, to express them on the surface of the microorganism. Then, the microorganism may be introduced into mineral dispersion (liquid in which mineral particles are dispersed).

An amount of introduction for a microorganism may be appropriately adjusted by considering certain conditions such as an amount of minerals dispersing in liquid. For an example of phage, in relative to 100 g/L of mineral particles, the amount of phage may be $10^{10}$ pfu/mL-$10^{18}$ pfu/mL, more preferably, $10^{11}$ pfu/mL or more, yet more preferably $10^{12}$ pfu/mL or more. The upper limit may be preferably $10^{16}$ pfu/mL or less, more preferably $10^{15}$ pfu/mL or less. Alternatively, in relative to 3 g/L of mineral particles, the amount of a phage may be $10^{17}$ pfu/mL-$10^{21}$ pfu/mL, more preferably, $10^{18}$ pfu/mL-$10^{20}$ pfu/mL.

Introducing a microorganism and then leaving a microorganism for a while, peptides on the surface of the microorganism bind to mineral particles to be aggregated and then to be precipitated. After this, the precipitated minerals on the bottom may be recovered.

5-3. A Method for Isolating by Column Chromatography

In one embodiment of the present invention, via column chromatography, a substance (specifically, arsenic-containing mineral, more specifically, enargite) may be isolated. In this procedure, initially, at least any one of the above-described peptides is affixed to a carrier by a technique known in the art. Then, the carrier may be introduced into a column for purification. After preparing the column, liquid in which a substance disperses is passed through the column. Then the substance binds to the inside of the column, and/or elution of the substance is delayed. Thereby, the substance of interest may be isolated.

5-4. A Method for Isolating by a Particle

In one embodiment of the present invention, using a particle, a substance (specifically, arsenic-containing mineral, more specifically, enargite) may be isolated. Initially, the above-described peptides may be affixed to the surface of the particle by a technique known in the art. Then, the particle may be introduced into mineral dispersion (liquid in which mineral particles are dispersed). Introducing the peptide-bound particle and then leaving it for a while, peptides on the surface of the particle bind to mineral particles to be aggregated and then to be precipitated. After this, the precipitated mineral on the bottom may be recovered. Alternatively, a particle may be a magnetic bead, and without waiting for precipitation, mineral particles may be recovered by magnetic power.

5-5. Method for Isolation Via Froth Flotation

In one embodiment, the method of the present invention may isolate, with use of a collector or a frother, certain substances (specifically, arsenic-containing minerals, more specifically, enargite). Specifically, a collector or a frother may be bound to the peptide of the present invention via a technique known in the art. Then the bound collector or frother may be introduced into solution to be agitated (other agents may be introduced if required) to produce bubbles. After that, mineral particles may be introduced to be trapped by bubbles. Thereby, mineral particles may be recovered. Alternatively, such a peptide may be bound to a chemical moiety that renders hydrophobicity (e.g. alkyl group, phenyl group, a hydrophobic amino acid, etc.) thereby working as a collector such that it may be prone to be trapped by a bubble.

In another embodiment, a peptide of the present invention may be used as a depressant. A depressant described herein refers to an agent for inhibiting certain minerals from floating in process of froth flotation.

Moreover, the peptide of the present invention may be integrated with microorganisms for its usage. More specifically, the peptide of the present invention may be used such that it exists on the surface of microorganisms. The microorganisms may include the ones as exemplified in the section of "4-1. Microorganism". One of preferable microorganisms is phage, more preferable is M13 bacteriophage.

Although the following descriptions do not intend to limit the scope of the present invention, a peptide of the present invention can hydrophilize the surface of arsenic-containing minerals (e.g. enargite), thereby enabling to inhibit the arsenic-containing minerals from being trapped by bubbles.

Thus, the present invention may be advantageous especially in separating from minerals that may be sorted to concentrate fraction (e.g., pyrite, chalcopyrite, etc.). In preferable embodiments, first, a peptide and/or a microorganism including a peptide may be introduced into mineral dispersion of arsenic-containing minerals (e.g. enargite) and then collector may be introduced. Introducing in such an order effectively can repress trapping arsenic-containing minerals with bubble.

Although not limited to certain conditions, froth flotation may be typically performed under the following conditions.

Pulp density 50-600 (dry-g/L)
Time for froth flotation 5-30 min
pH for froth flotation from 3 to 10
Collector 5-100 g/t (gram per ton of subject minerals)
Frother 0.001-100 g/t (gram per ton of solution for froth flotation)

An amount of peptide is not limited to a particular amount and an effective amount in view of a depressant may be appropriately determined under the above-described conditions for froth flotation. In case of using a microorganism comprising peptides, not peptides per se, an amount of a microorganism corresponding to the above may be used. For example, an amount of phage may be from $10^{10}$ pfu/L to $10^{18}$ pfu/L (from $10^{14}$ pfu/T to $10^{22}$ pfu/T).

Collector is an agent being able to selectively adsorb to the surface of minerals of interest thereby increasing hydrophobicity of its surface. Specific examples include, but are not limited to, collector which is commercially available for recovering sulfide copper minerals with higher priority, more specifically, xanthate, and thiocarbamate, and so on and a mixture thereof, yet more specifically, potassium amylxanthate, etc. The amount of collector may be from 5 to 100 g/t. If the amount is less than 5 g/t, it is difficult to obtain floated minerals (concentrate fraction), which is undesirable. If the amount is more than 100 g/t, its effect reaches a plateau and more amount will be meaningless. Meanwhile, in case where rough selection as a preliminary step (rougher circuit) is followed by refining minerals (cleaner circuit) which is via froth flotation with use of the peptide and/or microorganism including the peptide for separating arsenic-containing minerals from other minerals, it may be omitted to introduce a collector at the stage of refining minerals. This is because the collector already exists, originating from the rougher circuit.

A frother is an agent which is dissolved in a solvent to stabilize bubbles in solution. A specific example may include, but not limited to, Tween, methyl isobutyl carbinol (MIBC), pine oil, Aerofroth 70 (CYTEC), etc. An amount of a frother may be from 0.001 to 100 g/t. If the amount is less than 0.001 g/t, it is difficult to obtain floated minerals, which is undesirable. If the amount is more than 100 g/t, its effect reaches a plateau and more amount will be meaningless. Meanwhile, in case where rough selection as a preliminary step (rougher circuit) is followed by refining minerals (cleaner circuit) which is via froth flotation with use of the peptide and/or microorganism including the peptide for separating arsenic-containing minerals from other minerals, it may be omitted to introduce a frother at the stage of refining minerals. This is because the frother already exists, originating from the rougher circuit, as similar to a collector.

6. Selectivity for Binding to Mineral

The above-described peptides have selectivity in that they strongly bind to specific minerals, but do not bind to other minerals. More specifically, they can strongly bind to arsenic-containing minerals (e.g., enargite), but do not bind to other minerals (such as chalcopyrite) (alternatively, the degree of their binding for arsenic-containing minerals is significantly higher than those of other minerals). Thus, from a mixture of arsenic-containing minerals and other minerals, the above-described methods enable to separate and/or remove arsenic-containing minerals. Alternatively, the above-described peptide may be used for the purpose of identifying arsenic-containing minerals. For example, a detection marker (e.g., fluorescence molecule, etc.) can be bound to peptides of the present invention to detect arsenic-containing minerals.

Additionally, the above-described peptides can function as depressant even in the presence of collector and/or frother. In other words, the above-described peptides can hydrophilize the surface of certain minerals. Alternatively, the above-described peptides can retain ability of binding to certain minerals even in the presence of surfactants. More preferably, the above-described peptides can retain ability of selective binding to certain minerals even in the presence of surfactants. Since surfactants are frequently used in the process of froth flotation, this feature is advantageous for actual froth flotation. Surfactants can include anionic surfactants, cationic surfactants, amphoteric surfactants, non-ionic surfactants, etc, typically nonionic surfactants. One of examples for non-ionic surfactants may be Tween 20

7. A Method for Preparing Peptide

The above-described peptides may be prepared in various ways. DNA encoding at least any one of the above-described peptides may be introduced into an expression vector, and the vector may be introduced into a microorganism, etc., to express the peptides in a large scale to be recovered. Alternatively, in addition to a genetic engineering technique, the peptides may be prepared via an organic chemistry technique.

Alternatively, in case of preparing a phage (e.g., M13-phage) having at least any one of the above-described peptides on its surface, a phage display method may be available. A microorganism having a peptide of interest on its surface may be prepared by genetic engineering technique known in the art.

EXAMPLES

Now, via the following working examples, the above-described embodiments of the present invention are described more specifically, although the scope of the present invention is not limited to the following working examples.

(Example 1) Selection of a Enargite-Adsorbing Phage Via a Phage Display Method

For the purpose of screening peptides that can adsorb enargite, a phage display method was performed. Specifically, M13 bacteriophage library was constructed, in which peptides with 12 amino acids were randomly bound to phages. Using this library, enargite that was ground to the particle size of 75 micrometers or less was contacted with the library. Then, only bacteriophages that bound to enargite were recovered, and *E. coli* was infected with the recovered phages to grow the phages again. After that, the phages were contacted with enargite again, and only the adsorbed phages were recovered. These operations of adsorbing and recovering (panning) were repeated certain times. DNA sequences of the selected phages were analyzed to identify amino acids sequences binding to the phages.

At the screening, the pulp density of the contacted enargite was 3000 ppm and the panning was repeated 4 times. As a point of difference from the method as taught by Patent Literature 4 (WO2018/052134), surfactant (Tween (R)-20) was introduced with its concentration being increased for each of panning in the present screening (as for concentration, 0.1% for 1st panning, 0.5% for 2nd panning, 0.7% for 3rd panning, 1.0% for 4th panning). Thereby, samples having a higher ability of binding can be obtained and samples having an ability of non-specific binding to enargite can be effectively excluded. DNA sequences for the resultant phages were analyzed and the phages having peptide according to the following amino acid sequence were identified:

Ser-Leu-Asp-Gly-Ala-Gly-Ala-Ala-Leu-Arg-Thr-Ser (SEQ ID NO: 1)

Hereinafter, a phage being bound to the above peptide is referred to as A56-phage.

(Example 2) ELISA Analysis for Phages being Capable of Binding to Enargite

Using enargite and A56-phage that was screened in Example 1, an amount of binding to enargite was measured by ELISA method (Enzyme-Linked Immunosorbent Assay). Specifically, 3000 mg/L of enargite were suspended and then aliquoted to each well of 96-well microplate. Each phage was added into each well under the conditions of pH 7, and unbound phages were washed out. After that, an anti-M13-phage antibody conjugated with an enzyme (peroxidase) was added and then unbound anti-phage antibodies were washed out. Next, 2,2'-azino-bis (3-ethylbenzothiazoline-6-sulphonic acid) diammonium salt (ABTS), which is the substrate for the enzyme, was added. Blue-colored samples resulting from digestion of ABTS were analyzed by a microplate reader with a wavelength of 405 nm. Furthermore, the same procedure was performed with the replacement with the chalcopyrite.

As a result of calculating a ratio of binding ability of chalcopyrite to binding ability of enargite, the ratio of enargite:chalcopyrite was 4.5:2.5.

Thus, A56-phage was shown to bind more specifically to enargite than chalcopyrite. This shows that A56-phage is useful for selection of enargite in the co-presence of chalcopyrite and enargite.

(Example 3) Bubble Pickup Test Using Peptide (Enargite)

A56-phages of Examples 1 and 2 were used for bubble pickup test. Specifically, enargite was initially suspended by pure water such that its density was 100 g/L and pH was adjusted to 7. Additionally, MIBC as frother was also introduced (final concentration was 10 microL/L). Then, two types of samples were prepared. One was the suspension which 56-phage was introduced into (the ultimate density was 10^10 pfu/L-10^18 pfu/L). The other was the suspension without A56-phage. These samples were agitated by a vortex mixer for one minute and were left for five minutes. Then, after adding A56-phage, collector Xanthate was added. In another example, before adding A56-phage, collector Xanthate was added.

Figure 1:
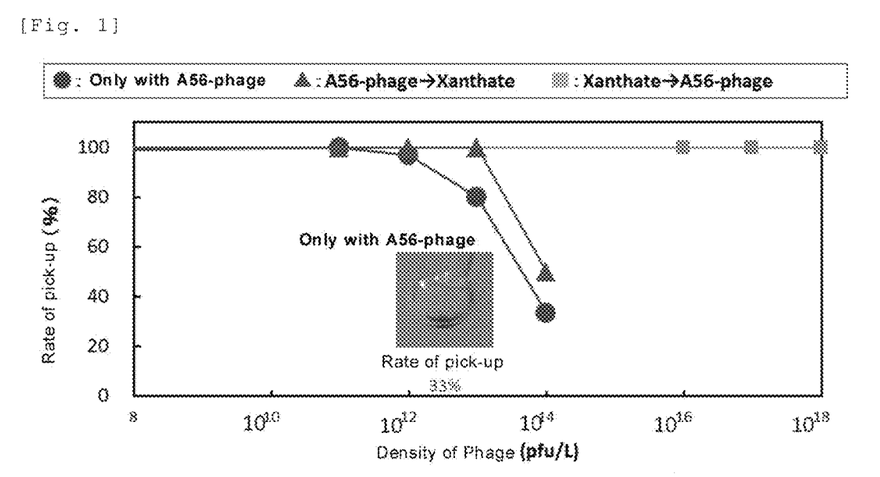
FIG. 1 shows results of bubble pick-up test by peptide according to one embodiment of the present invention.

20 microliter of a bubble was formed on tip of micropipette tip. Then, the bubble was contacted to the surfaces of the suspensions of the two samples for two seconds. The contacts were repeated 30 times. The probability of adhesion (rate of pickup) was calculated according to the following formula.

Rate of pickup (%)=(the number of times when minerals adhere/30)×100(%)

The results are shown in FIG. 1. It was shown that treating enargite by A56-phage significantly reduces adhesion to bubble. Furthermore, regarding the timing for collector, it was shown that adding after treating enargite with A56-phage was more effective, and further reduced adhesion to bubble.

(Example 4) Comparison Test for Ability of Binding by Peptide in the Presence of Surfactant The following two types of peptides were prepared. These peptides were conjugated with Fluorescein at N-terminal as a fluorescence labeling.

(1) Ser-Leu-Asp-Gly-Ala-Gly-Ala-Ala-Leu-Arg-Thr-Ser (SEQ ID NO: 1) (a peptide obtained from A56-phage, referred to as A56 peptide hereinafter)
(2) Asn-Pro-Glu-His-Ala-Ala-Phe-Ser-Pro-Val-Thr-Val (SEQ ID NO: 2)(a peptide obtained from A710-phage, referred to as A710 peptide hereinafter, see WO2018/052134)

Enargite was fixed to the bottom of 96-well plate (density of mineral was 3 g/L). Buffer containing a peptide was introduced into each well to make the peptide bind to enargite. Then, supernatant was aspirated, and each well was washed with buffer without a peptide three times. After washing, a measurement for fluorescence was done. Incidentally, the buffer was a citric acid buffer (the concentration was 50 mM) in which pH was adjusted to pH3. The concentration of the peptide in the buffer was adjusted to 100 ng/mL.

Two types of the buffer containing a peptide were prepared. Specifically, one is buffer with Tween20 and the other is buffer without Tween20.

Figure 2:
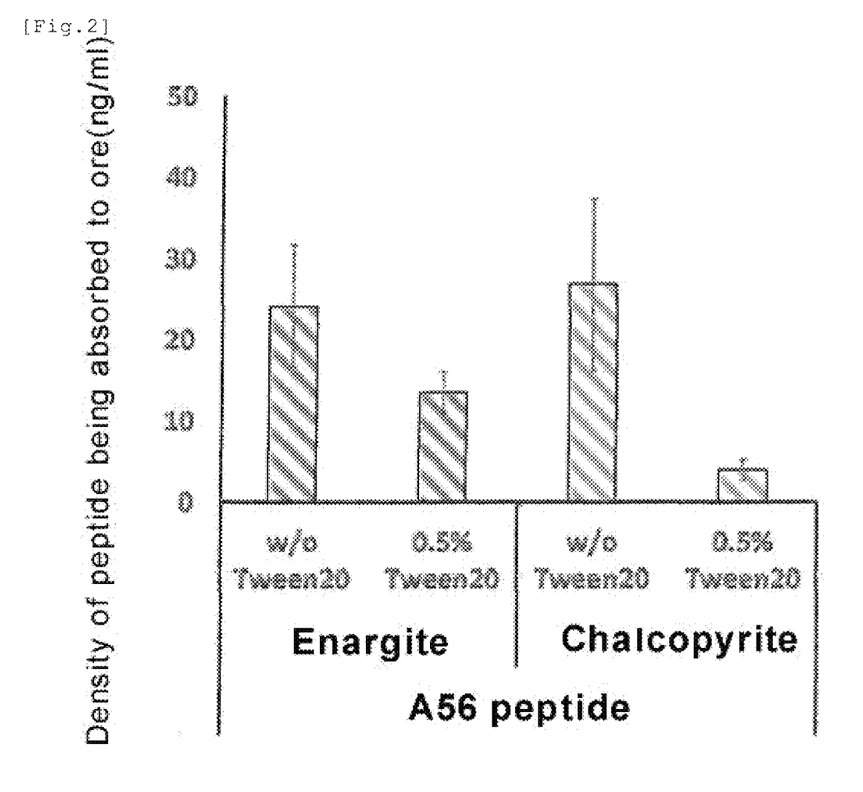
FIG. 2 shows an ability of binding by peptide according to one embodiment of the present invention.
Figure 3:
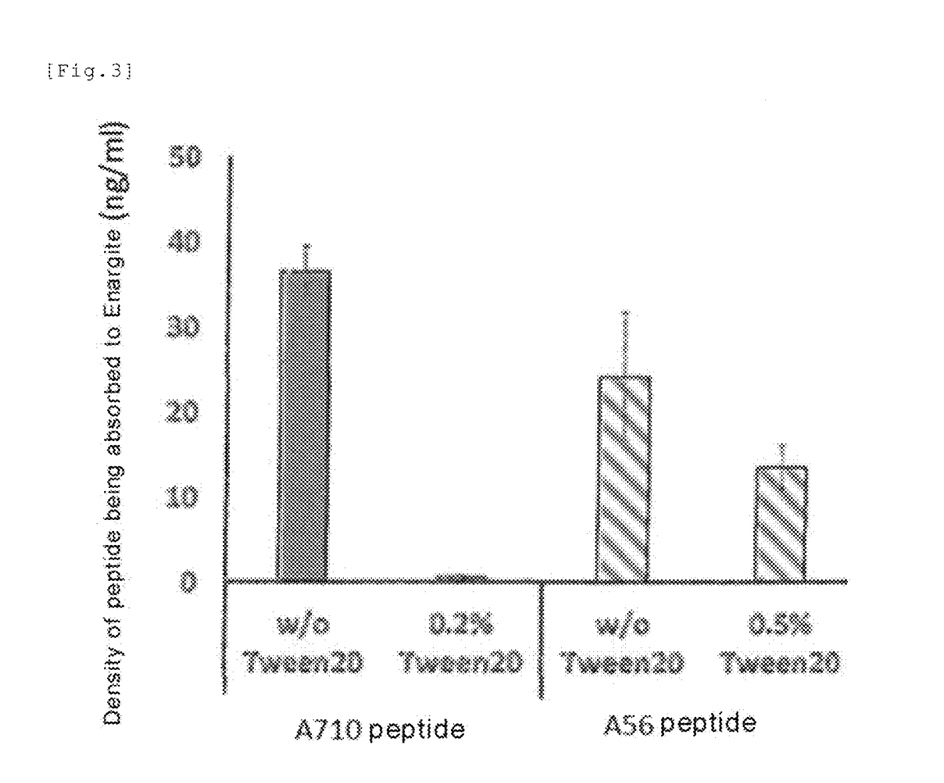
FIG. 3 shows an ability of binding by peptide according to one embodiment of the present invention.

The results were shown in FIG. 2 and FIG. 3. FIG. 2 shows that in the absence of Tween20, A56 peptide did not show selectivity to enargite, while in the presence of Tween20, A56 peptide shows selectivity of binding to enargite. Further, FIG. 3 shows that in the absence of Tween20, both of A710 peptide and A56 peptide show biding activity to enargite. In the presence of tween20, although both of the peptides show weaker ability of binding to enargite, A56 peptide was shown to retain stronger ability of binding to enargite comparing to those of A710 peptide. Comparing to the case of A710 peptide, an amount of Tween20 was higher in the case of A56 peptide, which was more severe conditions. Despite this, while ability of binding by A710 peptide was largely decreased, ability of binding by A56 peptide was retained. This data shows that A56 peptide was useful in froth flotation in which frother is used.

What is claimed is:

1. A method for isolating a mineral containing arsenic from a mixture of the mineral containing arsenic and chalcopyrite, the method comprising contacting a peptide with a mineral containing arsenic to make the peptide binding to the mineral,
wherein the peptide comprises the following sequence:

(SEQ ID NO: 1)
Ser-Leu-Asp-Gly-Ala-Gly-Ala-Ala-Leu-Arg-Thr-Ser.

2. A method of claim 1, the method comprising froth floating with use of the peptide, the froth floating comprising:
introducing the mixture;
introducing a surfactant;
introducing the peptide and/or the microorganism containing the peptide as a depressant, whereby the mineral containing arsenic is sorted to flotation tailings and the chalcopyrite is sorted to concentrate in the presence of the surfactant.

* * * * *

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Randomly synthesized peptide

<400> SEQUENCE: 1

Ser Leu Asp Gly Ala Gly Ala Ala Leu Arg Thr Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Randomly synthesized peptide

<400> SEQUENCE: 2

Asn Pro Glu His Ala Ala Phe Ser Pro Val Thr Val
1               5                   10
```